United States Patent
Edwards et al.

(10) Patent No.: US 7,012,426 B2
(45) Date of Patent: *Mar. 14, 2006

(54) HIGH-RESOLUTION HIGH-SPEED NMR WELL LOGGING DEVICE

(75) Inventors: Carl M. Edwards, Katy, TX (US); Daniel T. Georgi, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 43 days.

This patent is subject to a terminal disclaimer.

(21) Appl. No.: 10/765,611

(22) Filed: Jan. 27, 2004

(65) Prior Publication Data
US 2004/0183533 A1      Sep. 23, 2004

Related U.S. Application Data

(63) Continuation of application No. 09/870,287, filed on May 30, 2001, now Pat. No. 6,720,765.

(51) Int. Cl.
*G01V 3/00* (2006.01)

(52) U.S. Cl. .................. 324/303; 324/319
(58) Field of Classification Search ............ 324/303, 324/300, 318, 319, 320, 306
See application file for complete search history.

(56) References Cited

U.S. PATENT DOCUMENTS

| | | | | |
|---|---|---|---|---|
| 4,350,955 A | | 9/1982 | Jackson et al. | 324/303 |
| 4,408,161 A | * | 10/1983 | Brown | 324/303 |
| 4,714,881 A | | 12/1987 | Givens | 324/303 |
| 4,717,877 A | | 1/1988 | Taicher et al. | 324/303 |

(Continued)

FOREIGN PATENT DOCUMENTS

WO      WO01/07937 A1      1/2001

OTHER PUBLICATIONS

Jennifer R. Spadea, et al; *Optimization of Printed Coil Arrays for Microscopic Imaging and Spectroscopy*, Proceedings—19th International Conference—IEEE/EMBS Oct. 30-Nov. 2, 1997, pp. 454-466.

(Continued)

*Primary Examiner*—Louis Arana
(74) *Attorney, Agent, or Firm*—Madan, Mossman & Sriram, P.C.

(57) ABSTRACT

Wireline NMR well logging measurements suffer from disadvantages of poor vertical resolution, logging speeds less than 20 ft/min, and power consumption in excess of 200 W. In spite of these disadvantages, NMR well logging is used because it is capable of providing estimates for a number of petrophysical parameters that are difficult to obtain from other wireline data. These include estimates of the bulk volume irreducible (BVI) of fluids in the formation. The present invention targets BVI and clay bound water (CBW) measurements. Logging speeds of up to 60 ft/min are attainable with little or no loss of resolution. In one preferred embodiment, the tool has four sensors circumferentially distributed around the logging tool and in contact with the borehole wall. A horseshoe like magnet is used to generate the static magnetic field. The magnet poles are designed such that the magnetic field is uniform perpendicular tool motion, as well as provide a sufficiently large extent of the static field to provide polarization for bound water in rock formations. The RF portion of the sensor is comprised of at least one coil configured for transmission of an RF magnetic field into rock formations and at least two coils configured to separately receive the NMR signal from the formation. In another embodiment a coil is wound around the pole pieces or the iron yoke for the purpose of field shifting to enable acquisition of phase-alternated measurements.

49 Claims, 4 Drawing Sheets

U.S. PATENT DOCUMENTS

| | | | | |
|---|---|---|---|---|
| 5,055,787 | A | 10/1991 | Kleinberg et al. | 324/303 |
| 5,488,342 | A | 1/1996 | Hanley | 335/306 |
| 5,610,522 | A | 3/1997 | Locatelli et al. | 324/319 |
| 5,646,528 | A | 7/1997 | Hanley | 324/303 |
| 5,977,768 | A | 11/1999 | Sezginer et al. | 324/303 |
| 6,018,243 | A | 1/2000 | Taicher et al. | 324/303 |
| 6,023,164 | A | 2/2000 | Prammer | 324/303 |
| 6,173,793 | B1 | 1/2001 | Thompson et al. | 174/45 |
| 6,720,765 | B1 * | 4/2004 | Edwards et al. | 324/303 |

OTHER PUBLICATIONS

Fa-hsuan Lin et al.; *Quantitative Spatial/Spectral Analysis of Magnetic Resonance Imaging Surface and Phased Array Coils of Arbitrary Geometry Based on Method of Moment*, 18th Annual International Conference of the IEEE Engineering in Medicine and Biology Society, Amsterdam 1996, pp. 2281-2282.

Jay R. Porter et al.; *A 16-Element Phased-Array Head Coil*, 4th International Conference on Applications of Magnetic Resonance to Food Science, Sep. 7-9, 1998, pp. 272-279.

Cecil E. Hayes et al.; *Noise Correlations in Data Simultaneously Acquired from Multiple Surface Coil Arrays*, Magnetic Resonance in Medicine 16, 1990, pp. 181-191.

Chris D. Constantinides et al.; *Signal-to-Noise Measurements in Magnitude Images from NMR Phased Arrays*, Proceedings—19th International Conference—IEEE/EMBS Oct. 30-Nov. 2, 1997; pp. 456-459.

* cited by examiner

HIGH-RESOLUTION HIGH-SPEED NMR WELL LOGGING DEVICE

CROSS REFERENCES TO RELATED APPLICATIONS

This application is a continuation of U.S. Pat. application Ser. No. 09/870,287 filed on May 30, 2001, now U.S. Pat. No. 6,720,765.

BACKGROUND OF THE INVENTION

1. Field of the Invention

The invention is in the field of Nuclear Magnetic Resonance ("NMR") tools. More specifically, the invention pertains to new designs in NMR measuring devices in the application of oil well logging.

2. Description of the Related Art

Nuclear Magnetic Resonance has uses in many areas, including the fields of medicine, non-destructive testing, and in well logging in the oil exploration industry. In the well logging industry, NMR is used in determining properties such as porosity of the material, permeability, the bound liquid volume, the clay bound volume (CBW) and bulk volume irreducible (BVI), as well as formation type and oil content.

A simple NMR device used in well logging uses a permanent magnet to apply a static magnetic field to a desired volume of investigation. Many magnet arrangements and field geometries have been proposed in prior art. In U.S. Pat. No. 4,350,955 to Jackson et al., two cylindrical magnets are placed end to end with north poles facing each other and are separated by a gap. This configuration produces a field in the center of this gap which is extending substantially radially outward. There are other designs which include spatial arrangements of multiple magnets. U.S. Pat. No. 4,717,868 to Taicher et al. and U.S. Pat. No. 4,710,713 to Shtrikman et al. show side-by-side arrangements of multiple magnets in order to design regions of magnetic fields where the field lines are substantially perpendicular to the longitudinal direction of the device.

The principle of NMR works because atomic nuclei contain magnetic moments associated with their nuclear spin. In the absence of an applied magnetic field, thermal fluctuations cause these moments to have random orientations in space. When these nuclei are subjected to a static magnetic field, the magnetic moments tend to align either parallel or anti-parallel to this applied field.

The permanent magnet of the NMR tool establishes the direction of orientation of the magnetic moments in a region being investigated. Typically in the art, a transmitter coil is placed in this region in order to induce a RF magnetic flux into this region by means of the circuitry to which it is attached. The transmitter coil is oriented such that the magnetic field it induces into the volume lies substantially in the plane that is perpendicular to the static magnetic field. A receiver coil is also placed in this region. In prior art, the transmitter coil and the receiver coil are the same. If the transmitter coil is separate from the receiver coil, the magnetic field produced by the coils must still be substantially perpendicular to the static field, but the coils need not share the same orientation. By applying a RF magnetic field perpendicular to the direction of the static field, we can "flip" the nuclear spin vectors out of their alignment with the static field.

Typically in the art, the transmitter coil induces a RF magnetic pulse whose duration is timed to reorient the magnetic moments of the nuclei along a direction that is perpendicular to both the direction of the static field of the permanent magnet and to the direction of the applied RF pulse. Once the spin moments are perpendicular to the static field and the RF pulse is removed, the moments undergo two notable processes. Firstly, the spins will realign along the direction of the static magnetic field. This decay back along the direction of the static field occurs over a characteristic time scale called the spin-lattice relaxation rate, $T_1$. Secondly, since the magnetic moments are non-aligned with the static field, they experience a perpendicular force which causes them to precess around the static field. The rate of precession is known as the Larmor frequency and is proportional to the strength of the static field.

Immediately following the application of the "flipping" RF magnetic field, the spin vectors are all pointing in the same direction, and ideally as they precess, they should continue to point in a common direction. In real situations, the strength of the static field is inhomogeneous in space. As a result, the spins will tend to precess at different rates. The different precession rates cause the vector sum of the magnetization in the plane of the spins to decay to zero. This decay of the spin magnetization in the plane perpendicular to the static field is known as the free induction decay (FID) and is characterized by its decay rate, $T_2^*$. A simple method comprised of another magnetic pulse with twice the duration of the first pulse flips the spin vectors 180 degrees. After the flip, the leading spins now find themselves behind the other spins and the lagging spins find themselves at the front of the diffusion. As a result, the magnetization vectors begin to reconverge. At some later time, all the spin vectors are aligned again in the same direction. This realignment creates a "spin echo" which can be recorded as an induced voltage in the receiver coil. As the time between the excitation pulse and the realignment pulse is increased, the spin echo amplitude decays. Neglecting microscopic molecular diffusion, the characteristic decay time is known as the spin-spin or transverse relaxation time and is denoted as $T_2$. The amplitude of the spin echoes can be used to determine spin density, $T_1$ and $T_2$.

Oil-based muds are becoming increasingly prevalent in borehole drilling techniques. Current methods of determining dip formation, such as electrical resistivity sensors, do not operate well in the presence of these oil-based muds. NMR techniques, however, can work in an environment containing oil-based muds. In normal NMR procedures, the logging process is slower than more conventional methods. Power consumption is excessive, often more than 200 W. However NMR remains useful because it gives information on petrophysical parameters that otherwise are unobtainable.

A smaller device could use less material and less energy than current commercial devices. The invention described herein concerns itself with BVI and CBW measurements only. Due to the nature of these measurements, which can be performed closer to the device, the sensor itself can be is smaller. Reducing size cuts material and energy costs, and simultaneously improves the sensitivity and resolution of the machine. With the increased sensitivity, the logging speeds can also increase, thereby reducing costs further.

Reduced size also allows the device to be placed on a sensor assembly which can be placed to the side of the tool. The invention further introduces a multiple receiver coil assembly which creates a high-resolution log.

SUMMARY OF THE INVENTION

The present invention is a logging tool for nuclear magnetic resonance (NMR) logging of an earth formation. One or more sensor assemblies are coupled to the housing of the logging tool by an arm, enabling close contact with the borehole wall. The static magnetic field is produced by a horseshoe or U-shaped magnet. Separate transmitter and receiver coils are used for pulsing the formation with a radio frequency (RF) field and receiving spin-echo signals. Short CPMG sequences or modified CPMG sequences having a refocusing angle of less than 180° may be used for the RF pulsing. This makes it possible to obtain estimates of CBW and BVI. High logging speeds are possible because of the short pulse sequences.

To further increase the logging speed, the axial extent of the transmitter coils and the permanent magnet is greater than that of the receiver coils. This ensures that the received signals correspond to substantially equal polarization of the nuclear spins even at high logging speeds.

When a plurality of sensor assemblies are used, azimuthal information about the parameters of interest is obtained. The arms are independently extendable and may be powered by a spring, hydraulic or electrical power. Differences of dip between the CBW and BVI are indicative of cross-bedding in the formation.

In a preferred embodiment, the U-shaped magnet includes two bar magnets connected at one end by a magnetically permeable core. Resolution of the device may be changed by altering the gap in the U-shaped magnet. Optionally, a coil around the core may be used as a field shifting electromagnet that makes possible the use of phase-alternated pulse sequences with little decrease in logging speed. When two or more receiver coils are used in a single sensor assembly, improved resolution is obtained using the phase of the received signals.

DESCRIPTION OF PREFERRED EMBODIMENT

Figure 1:
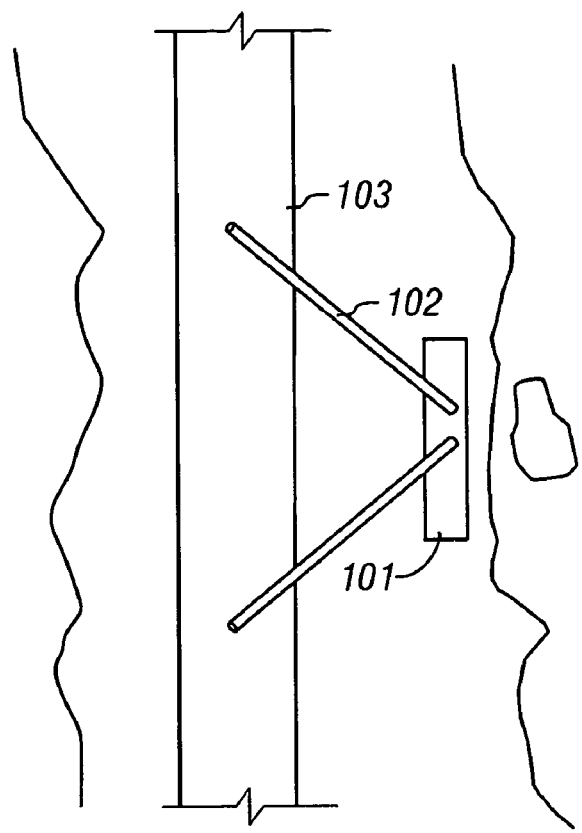
FIG. 1 shows a simplified side section of a logging tool, showing one sensor connected to the housing of the tool.

Referring to FIG. 1, the embodiment of the invention described herein is housed within a sensor assembly 101 which is attached by an arm mechanism 102 to the body 103 of the logging tool. The methods for attachment are the same as those which are commonly used in the well logging industry. The arm may be extended to make contact with the borehole wall using hydraulic, spring operated or electrical power. Although FIG. 1 displays only one sensor assembly, embodiments of the invention are not limited to only one sensor attachment. In fact, only the size of the sensor limits the number of sensors that can be used in a given embodiment.

Figure 2:
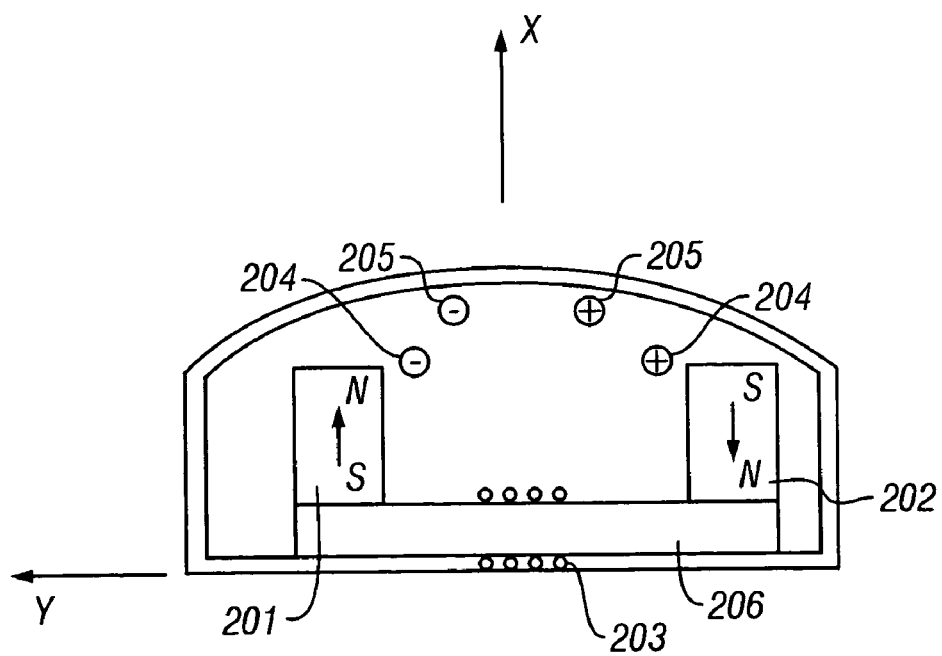
FIG. 2 shows a cross-sectional view of the sensor, showing the magnet system and coil assemblies.

As shown in FIG. 2, the sensor assembly comprises of a pair of magnets 201, 202 attached to an iron yoke 206, a transmitter coil assembly 204, a receiver coil assembly 205, and a coil 203 running lengthwise along the iron yoke. The coil 203 is intended to regulate the regions of magnetic field induced by the permanent magnets and may be referred to as a field shifting magnet. The magnet assembly is comprised of two bar magnets whose lengths typically are substantially longer than their width or height. The poles of the magnets are oriented along one of the shorter dimensions, hereafter referred to as the height. As shown in FIG. 2, the north pole of one magnet 201 is attached to a highly permeable iron yoke 206 and the south pole of the other magnet (202) is attached to the same yoke. A gap is left between the poles of the opposing magnets, causing the assembly to resemble a horseshoe magnet. The length of the magnets is oriented parallel to the axis of the logging tool. Consequently, the magnetic field is uniformly perpendicular to the direction of the tool motion. In the local coordinate system shown in FIG. 2, the static magnetic field points along the y-direction, which is generally but not necessarily considered to be the direction tangential to the circumference of the tool, while the z-direction is in the vertical, or longitudinal, direction. This geometry provides a sufficiently large extent of the static field to polarize the bound water in rock formations.

The magnet configuration described above is horseshoe or U-shaped. The yoke forms the base of the U. The horseshoe magnet design is a novel feature of the invention, having certain advantages over prior art. As one advantage, the gap between the two poles of the magnet assembly can be adjusted. When the length of the gap is shortened, the sensitive region under investigation moves in toward the magnet faces. Since the invention is intended for use in BVI and CBW measurements, the measurements can be taken in a region which lies closer to the device. Moving the sensitive region closer to the device thereby allows the embodiment of the invention to be smaller and thus require less material for construction.

In one embodiment of the invention, a coil (203) is wrapped around the yoke running lengthwise along the z-axis through the gap between the magnets. Through attached circuitry, a DC pulsed voltage induces a magnetic field in the coil substantially in the y-direction in the sensitive region, alternating parallel or anti-parallel to the direction of the magnetic field of the horseshoe magnet. The superposition of the induced magnetic fields from coil (203) with the static magnetic field of the horseshoe magnet allows for the creation of two separate sensitive volumes, which can then be excited in sequence in order to allow for data to be acquired in phase alternated pairs. This added functionality to the embodiment of the invention improves the resolution in the vertical direction and helps to remove sources of error.

The transmitter coil (204) is located away from the yoke near the outer faces of the horseshoe magnet configuration and is oriented in a plane perpendicular to the x-axis. A RF voltage applied to this coil induces a magnetic field substantially along the x-axis in the sensitive region.

The receiver coil assembly is oriented in the same direction as the transmission coil assembly. It is the intention of the design that the receiver coil assembly is slightly offset from the transmission coil and away from the magnet assemblies. The ability to offset the receiver coil from the transmission coil has the advantage of improving receiver sensitivity and of reducing coupling between the two coils. This offset is better illustrated in FIG. 3.

Figure 3:
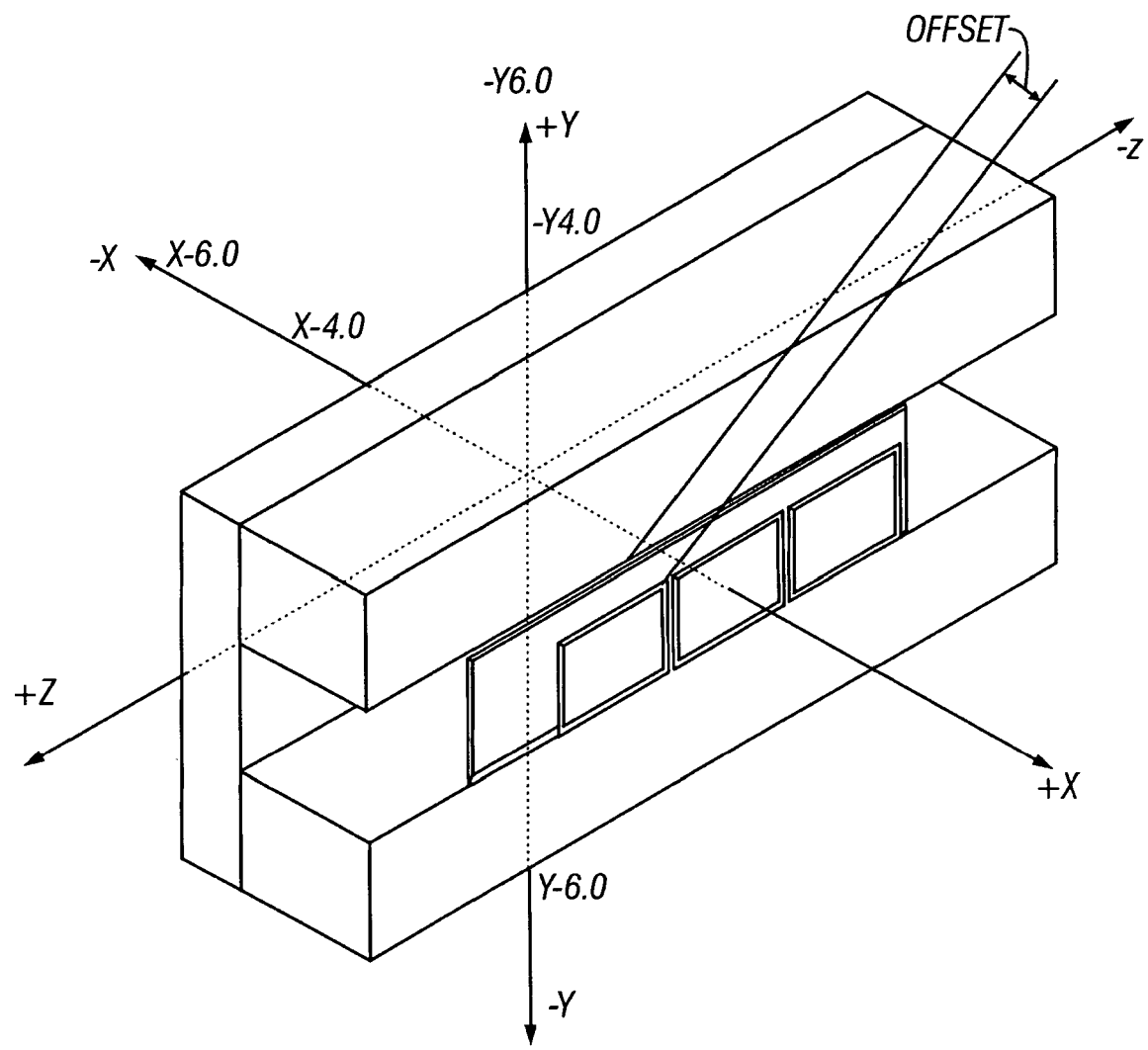
FIG. 3 shows a parallel view of the magnet system and the RF coils.

As can be seen in the parallel view of the sensor assembly shown in FIG. 3, the receiver coil assembly is designed to be a set comprised of two or more coils rather than only one coil. Multiple receiver coils are an innovation over prior art and allows the user a greater flexibility. The gap between the two or more receiver coils can be adjusted, even to the point where coils overlap. Adjusting the gap allows one to obtain optimal coupling between the receiver coils.

The signals from the receiver coil are digitized individually and combined to generate a resolution of approximately one inch. Each sensor on the tool will have its own electronics and be controlled by a master computer. Since the receiver coils on each sensor will have different yet determinable physical locations in the sensor, the phase of the NMR signal received by each receiver coil will be different by a determinable amount. It is possible, therefore, to combine the signals, using the proper phase relationship, and thereby to improve the resolution and the signal-to-noise ratio of the signal. This has been done routinely in medical imaging but has not been applied previously in wellbore logging instruments. See, for example, Hayes, C. and P. B. Roemer (1990); Lin, F.-h., S.-K. Jeng, et al. (1996); Constantinides et al.

It is the intention of the design that the transmission coil is longer along the z-axis than the full possible extent of the receiver coils. Separating the transmission coil and the receiver coil from each other, and simultaneously increasing the overall area of the transmission coil over that of the receiver coil overcomes many prior constraints. As an example, in prior art, a single coil acts as transmitter and receiver and cycles from one mode of operation to the other. In this prior design, when the coil is in receiver mode, substantial amounts of fluid which have not been excited by the initial pulse in the cycle can move into the sensitive region. As a result, some of the nuclei observed during the receiving portion of the cycle are not properly oriented and become a source of error. This error becomes greater as the longitudinal speed of the NMR device allowing more untreated spins to move into the region. As a result, this phenomenon imposes a practical upper limit to the effective logging speed of prior art. Separating the roles of the transmission and receiver cycles addresses this problem.

In the present design, the volume effected by the transmission coil is always larger than the sensitive volume examined by the receiver coil. Consequently, spins have a greater opportunity to be excited by the transmission coil before entering the sensitive region of the receiver coil. Increasing the number of excited spins allows for a new flexibility with respect to the logging speed, such that the NMR tool can be moving faster during logging.

Logging speeds can increase, because bound waters typically have $T_l$ relaxation times substantially less than 200 msec. This time scale is much less than that of light oils and gases which can have $T_l$ relaxation times of several seconds. The design criterion is quantified by the equation $$G_z v T_A << 2 B_1$$

where $G_z$ is the magnetic field gradient in the vertical direction, v is the speed of the tool, $T_A$ is the signal acquisition time, and $B_1$ is the strength of the RF magnetic field at the sensitive volume during the pulses. The expression quantifies the requirement that spins excited by the initial pulse of the acquisition sequence remain in the sensitive volume throughout the measurement. Bringing the sensitive region close to the magnetic faces increases $B_1$ by an order of magnitude over current commercial tools. Also, $T_A$ is decreased by a factor of two to five over current commercial tools. As a result, the design considerably relaxes restrictions on the product of $G_z$ and v over prior art. These constraints have limited previous inventions to quasi-two dimensional sensor designs. With the relaxed constraint, this invention can employ full three-dimension sensor designs. The relative sizes of the receiver and transmitter coils can be adjusted to fit desired resolution and maximum logging speeds.

The invention specializes in taking bound volume irreducible (BVI) and clay bound water (CBW) measurements. When the chief design criterion of the NMR tool is restricted to investigating these bound fluid volumes, then full advantage can be taken of the novel designs and features discussed above. Since immovable fluids typically have short relaxation times, data acquisition times can be reduced drastically, and logging speeds can be increased. Normal commercial wireline NMR logging tools have a logging speed less than 20 ft/min and usually less than 10 ft/min. Hydrocarbon identification logs can run as slow as 3 ft/min. The present invention can obtain logging speeds from somewhere between 40 ft/min and 60 ft/min. With this increased flexibility in speed, it is also possible to operate an embodiment of the device at a combination of multiple frequencies and slower logging speed, thereby obtaining high-resolution full spectrum data about the rock formation.

Also, by restricting measurements to those of bound fluids, which can be taken with small depth of investigation, the invention can be much smaller than prior art. The invention is designed to operate with a smaller depth of investigation, thereby increasing the sensitivity of the receiver coil and reduces the necessary size and mass of the permanent magnet. Typically, the depth of investigation can be reduced from 3 inches to 1 inch. Consequent to the reduction in size and mass, this sensor assembly can be carried as a unit on the side of the tool. This new ability to locate the sensors assembly to the side of the logging tool is a novel feature over prior NMR devices in which the permanent magnet is coaxial with the logging tool.

An embodiment of the invention allows for the ability to create azimuthal images of the borehole, providing greater detail. Utilizing many sensors gives this invention an advantage over prior art. Multiple sensors can be arrayed along the circumference of the borehole logging tool. In a preferred embodiment for this purpose, the tool has four sensors extending around the circumference of the tool, each of which can be placed against the wall of the borehole. Measurements made by the individual sensors may be analyzed to give relative dip information using known methods. Further detail can be achieved by rotating the sensor assembly by 90°, thereby orienting the assembly tangentially to the logging tool. This is shown in FIG. 3 where the sensor is rotated so that the y-axis is now parallel to the tool axis and the direction of motion while logging is along the y-axis. The z-axis of sensor may be deformed into an arc so that the sensor front more closely conforms to the borehole wall when pressed against it. The multiple (three are shown) receiver coils are now spaced along the circumference of the borehole and provide azimuthal resolution. As an example, for an 8.5-inch borehole, a sufficient imaging device would require four sensor assemblies, with six coils per sensor, with each coil being one inch in length. An azimuthal sensing capability is taught in U.S. Pat. No. 5,977,768 to Sezginer et al in the context of a measurement-while-drilling tool. Measurements are made over a limited circumferential sector. This makes it possible in near horizontal boreholes to differentiate between two proximate beds with different porosities. The Sezginer device does not, however, have the resolution of the present invention and is not designed for high speed logging.

An embodiment of the invention with a multiple arm assembly of three of more sensors can further take advantage of its azimuthal imaging capability to determine dip estimates. Dip results that are estimated from bound water, CBW, BVI calculation typically may yield different values, which can then indicate cross-bedded formations. As an example, a formation might contain fine and coarse grain sand formations layered with shale laminations. Dip estimates from BVI measurements would indicate the apparent orientation of the sand beds, while CBW measurements would indicate the apparent orientation of shale laminations. A minimum of three sensor assemblies is needed to determine the dip and azimuth of the sand beds and the shale laminations. True dip can be determined by combining this data with tool and borehole orientations. Devices and methods for determining tool and borehole orientations would be known to those versed in the art and are not discussed further.

Although FIG. 3 displays no variations in the magnetic material, this is not a necessary condition for the invention. It is envisioned that the geometry and material properties of the magnet might vary along any direction. Materials with higher magnetization may be used at the ends of the magnet assembly along the z-axis in order to reduce the vertical static magnetic field gradient and to ensure proper fluid magnetization. Variations of the magnet along x- and y-directions can be used to tune the x- and y-gradients of the field. Also, a practitioner of the art can vary the magnet properties in order to tune the magnetic field in the sensitive volume to the desired value.

Figure 4A:
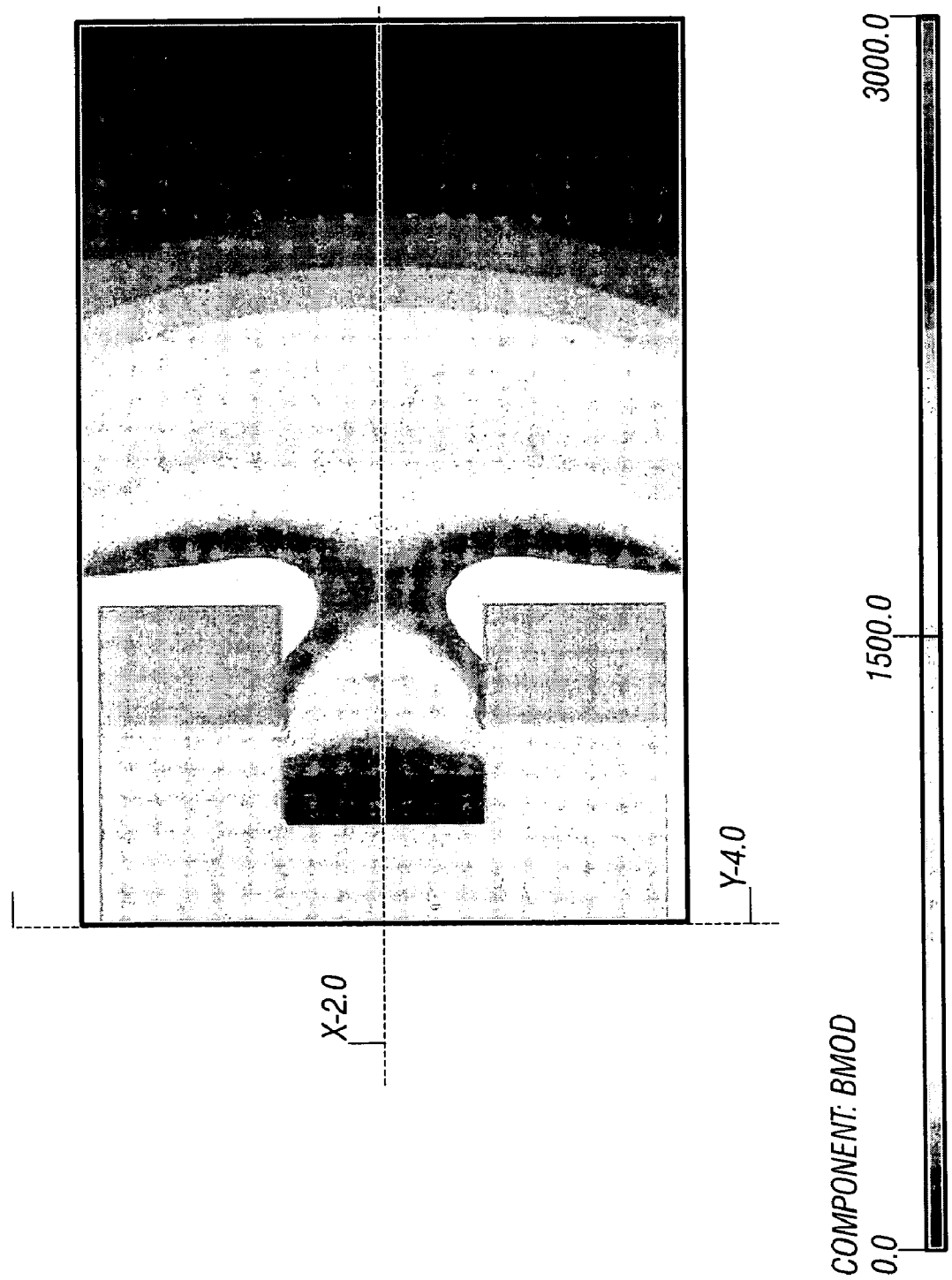
FIG. 4a shows a cross-sectional view of the static magnetic field distribution where the remnant magnetic field of the magnetic materials is 10,000 G.
Figure 4B:
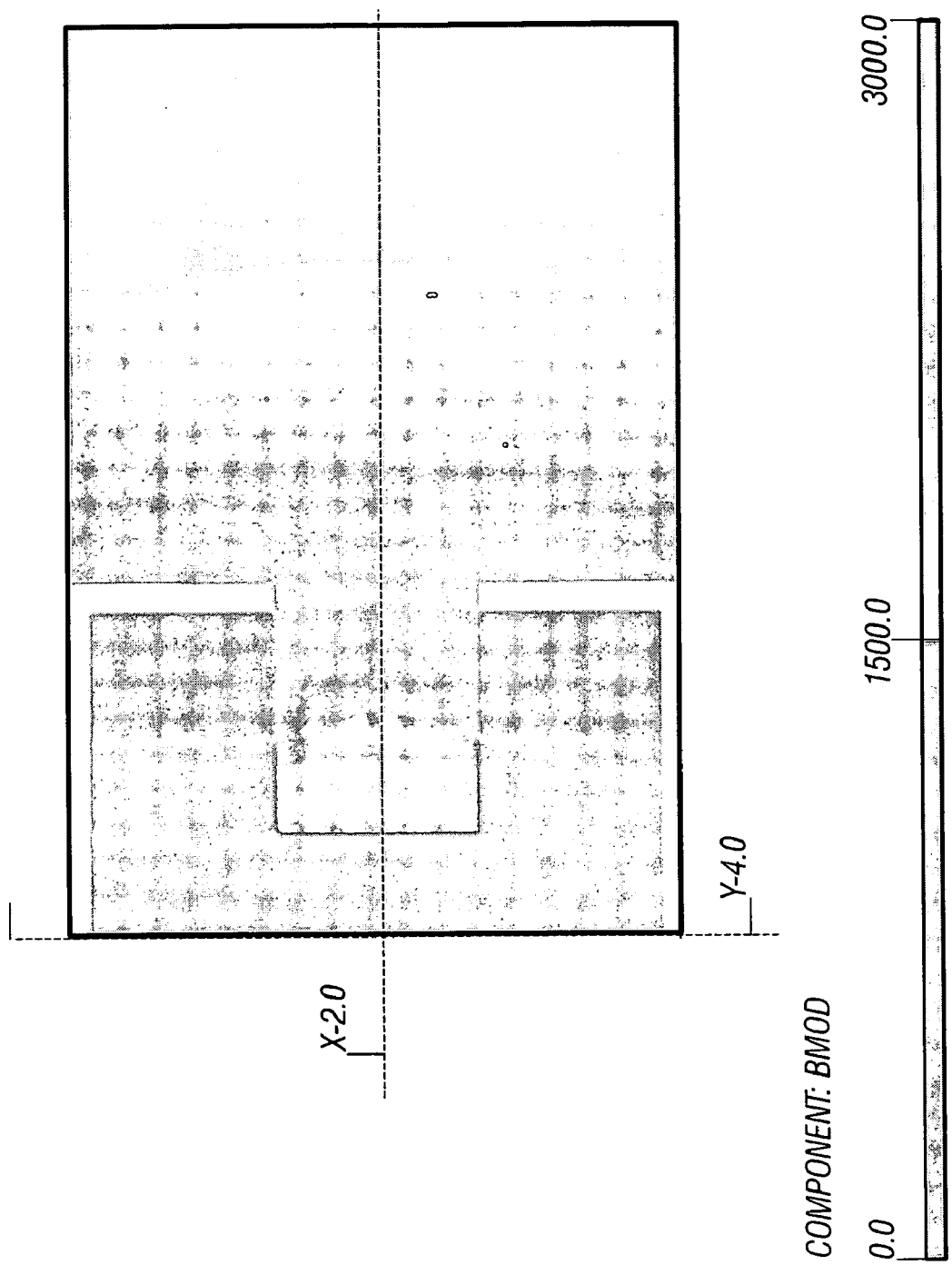
FIG. 4b shows a cross-sectional view of the static magnetic field distribution where the remnant magnetic field of the magnetic materials is 2,600 G.

FIG. 4a shows the field distribution for a magnetic material whose remnant magnetic field is 10,000 G. The field is one that can be produced by a Samarium-Cobalt magnet. FIG. 4b shows a similar configuration as in FIG. 4a with magnetic material having a remnant magnetic field of 2,600 G. The field is one that can be produced by Samarium-Cobalt or ferrite. The size of the gap in FIG. 4b is the same as in FIG. 4a.

It should be noted that there is a region along the x-axis in FIG. 4a near the face of the magnets where the iso-field lines change from being concave along the negative x-direction to being concave along the positive x-direction. Thus there is an optimum region along the x-axis where iso-field lines are straight. The position of this region of flat iso-lines along the x-axis is dependent solely on the arrangement of the magnets, (201) and (202), in FIG. 2. More specifically, this position depends on the size of the gap between these two magnets. Reducing the gap will move the flat region closer to the magnet faces and hence closer to the transmission and receiver coil assemblies. Positioning this region closer to the coils increases the accuracy of the signals. Adjusting the tool operating frequency can maximize the sensitive volume.

The device of the present invention may be used with any one of several pulsing techniques for the determination of BVI and CBW. As noted above, the rapidly relaxing components of the $T_2$ spectrum may be used for determination of these quantities. These rapidly relaxing components may be determined using CPMG sequences with different interecho times as well as the modified CPMG sequence with reduced power requirements taught by Reiderman et al. in U.S. Pat. No. 6,163,153.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A logging tool conveyed in a borehole for nuclear magnetic resonance (NMR) logging of an earth formation comprising:
    (a) a housing defining a longitudinal axis of the tool;
    (b) at least one sensor assembly coupled to the housing by a coupling device, a body of said at least one sensor assembly capable of being close to a wall of a borehole in the earth formation, said sensor assembly including
        (A) a magnet which provides a static magnetic field in a sensitive region in said formation,
        (B) a transmitter coil which produces a pulsed radio frequency (RF) magnetic field in said sensitive region, and,
        (C) at least one receiver coil which receives signals from nuclei in said sensitive region, said at least one receiver coil having an axis substantially parallel to an axis of said transmitter coil
    wherein an axial extent of the transmitter coil is greater than an axial extent of the at least one receiver coil.

2. The logging tool of claim 1 wherein said at least one sensor assembly further comprises a plurality of sensor assemblies circumferentially distributed about said housing.

3. The logging tool of claim 1 wherein said coupling device is operated by one of (i) a spring, (ii) hydraulic power, and, (iii) electrical power.

4. The logging tool of claim 1 wherein said magnet is a U-shaped magnet and further comprises:
    (i) a first magnet and a second magnet having a magnetization direction perpendicular to said longitudinal axis of the tool comprising arms of the U, said first and second magnets having opposite directions of magnetization, and
    (ii) a magnetically permeable yoke forming the base of the U.

5. The logging tool of claim 1 wherein said RF magnetic field is produced by activating the transmitter coil with one of (i) a CPMG sequence, and, (ii) a modified CPMG sequence having a refocusing angle less than 180°.

6. The logging tool of claim 4 wherein a gap between ends of the first and second magnet away from the yoke is adjustable.

7. The logging tool of claim 1 wherein the at least one receiver coil further comprises at least two receiver coils offset along the longitudinal axis.

8. The logging tool of claim 7 further comprising a processor for using the signals from the at least two receiver coils for determining a parameter of interest of the earth formation.

9. The logging tool of claim 7 wherein said at least one sensor assembly is adapted to be rotated to a position wherein said at least two receiver coils are at substantially the same longitudinal position.

10. The logging tool of claim 1 further comprising a field shifting electromagnet including a coil which adjusts a position of the sensitive region.

11. The logging tool of claim 1 wherein the at least one receiver coil is displaced towards the borehole wall from the transmitter coil.

12. The logging tool of claim 1 further comprising a processor which determines from the signals from the at least one receiver coil a parameter of interest of the earth formation.

13. The logging tool of claim 12 wherein the parameter of interest is at least one of (i) clay bound water, and, (ii) bulk volume irreducible.

14. The logging tool of claim 1 wherein said magnet has a higher magnetization at an end than at a middle portion of said magnet.

15. A sensor assembly for nuclear magnetic resonance (NMR) measurements from a medium comprising:
(a) a U-shaped magnet including a pair of magnets having opposed magnetization coupled by a permeable yoke providing a static magnetic field in a sensitive region in the medium;
(b) a transmitter coil producing a pulsed radio frequency (RF) magnetic field in said sensitive region; and,
(c) at least two spaced apart receiver coils which receive signals from nuclei in said sensitive region, said at least two receiver coils having axes substantially parallel to an axis of said transmitter coil.

16. The sensor assembly of claim 15 wherein said RF magnetic field is produced by activating the transmitter coil with one of (i) a CPMG sequence, and, (ii) a modified CPMG sequence having a refocusing angle less than 180°.

17. The sensor assembly of claim 15 further comprising a field shifting electromagnet including a coil which adjusts a position of the sensitive region.

18. The sensor assembly of claim 15 wherein said transmitter coil is positioned between the at least one receiver coil and the permeable yoke.

19. The sensor assembly of claim 15 wherein a gap between ends of the first and second magnet away from the yoke is adjustable.

20. The sensor assembly of claim 15 further comprising a processor which determines from the signals from the at least two receiver coils a parameter of interest of the earth formation.

21. A method of determining a parameter of interest of an earth formation comprising:
(a) conveying a logging tool having a longitudinal axis in a borehole in the earth formation;
(b) using a U-shaped magnet on at least one sensor assembly for producing a static magnetic field in a sensitive region in said formation, said at least one sensor assembly coupled to a housing of the logging tool by an coupling device;
(b) using a transmitter coil on the at least one sensor assembly for producing a pulsed radio frequency (RF) magnetic field in said sensitive region; and,
(c) using at least one receiver coil on the at least one sensor assembly for receiving signals from nuclei in said sensitive region, said at least one receiver coil having an axis substantially parallel to an axis of said transmitter coil.

22. The method of claim 21 wherein said at least one sensor assembly further comprises a plurality of sensor assemblies circumferentially distributed about said housing; the method further comprising obtaining information about an azimuthal variation of said parameter of interest.

23. The method of claim 22 wherein the plurality of sensor assemblies comprises three, and wherein the parameter of interest comprises bound volume irreducible, the method further comprising determining a dip and azimuthal direction of the formation.

24. The method of claim 22 wherein the plurality of sensor assemblies comprises three, and wherein the parameter of interest comprises clay bound water, the method further comprising determining a dip and azimuthal orientation of shale laminations.

25. The method of claim 22 wherein the plurality of sensor assemblies comprises three and wherein the parameter of interest comprises clay bound water and bulk volume irreducible, the method further comprising determining dip and cross-bedding of the formation.

26. The method of claim 21 further comprising operating the coupling device by one of (i) a spring, (ii) hydraulic power, and, (iii) electrical power.

27. The method of claim 21 wherein said U-shaped magnet further comprises:
(i) a first magnet and a second magnet having a magnetization direction perpendicular to said longitudinal axis of the tool comprising arms of the U, said first and second magnets having opposite directions of magnetization, and
(ii) a magnetically permeable yoke forming the base of the U.

28. The method of claim 21 wherein producing said pulsed RF magnetic field further comprises modulating a RF signal by one of (i) a CPMG sequence, and, (ii) a modified CPMG sequence having a refocusing angle less than 180°.

29. The method of claim 21 wherein said RF magnetic field has a field direction substantially orthogonal to said longitudinal axis and to a direction of the static magnetic field in said sensitive volume.

30. The method of claim 21 wherein the at least one receiver coil further comprises at least two receiver coils offset along the longitudinal axis.

31. The method of claim 30 further comprising using a processor for determining from the signals from the at least two receiver coils the parameter of interest of the earth formation.

32. The method of claim 30 further comprising:
(i) rotating said sensor assembly to position said at least two receiver coils at substantially the same longitudinal position; and
(ii) obtaining said signals with an increased azimuthal resolution.

33. The method of claim 21 further comprising using a field shifting electromagnet including a coil for adjusting a position of the sensitive region in the formation.

34. The method of claim 33 further comprising repeating steps (a)–(c) for a different positions of the sensitive region using a phase alternated pulse sequence.

35. The method of claim 21 wherein the transmitter coil has a greater length along the longitudinal axis than the at least one receiver coil, the method further comprising moving the logging tool along the longitudinal axis while making continuing measurements.

36. The method of claim 21 further comprising adjusting a gap between ends of the first and second magnet away from the yoke and adjusting a position of the sensitive region.

37. The method of claim 21 further comprising using a processor for determining from the signals from the at least one receiver coil the parameter of interest of the earth formation.

38. The method of claim 21 wherein the parameter of interest comprises at least one of (i) clay bound water, and, (ii) bulk volume irreducible.

39. The method of claim 38 wherein producing said pulsed RF magnetic field further comprises modulating a RF signal with a modulating signal that is one of (A) a CPMG sequence, and, (B) a modified CPMG sequence having a refocusing angle less than 180°.

40. The method of claim 39 wherein said modulating signal includes short interecho spacings for determining a rapidly decaying component of a $T_2$ distribution.

41. A method of determining a parameter of interest of a medium comprising:
(a) using a U-shaped magnet including a pair of magnets with opposed polarization coupled by a magnetically permeable yoke for producing a static magnetic field in a sensitive region in the medium;
(b) using a transmitter coil for producing a pulsed radio frequency (RF) magnetic field in said sensitive region; and,
(c) using at least two receiver coils having axes substantially parallel to an axis of said transmitter coil for receiving signals from nuclei in said sensitive region.

42. The method of claim 41 wherein producing said pulsed RF magnetic field further comprises modulating a RF signal by one of (i) a CPMG sequence, and, (ii) a modified CPMG sequence having a refocusing angle less than 180°.

43. The method of claim 41 wherein said RF magnetic field has a field direction substantially orthogonal to said longitudinal axis and to a direction of the static magnetic field in said sensitive volume.

44. The method of claim 41 further comprising using a field shifting electromagnet including a coil for adjusting a position of the sensitive region in the formation.

45. The method of claim 44 further comprising repeating steps (a)–(c) for a different position of the sensitive region using a phase alternated pulse sequence.

46. The method of claim 41 further comprising adjusting a gap between ends of the first and second magnet away from the yoke and adjusting a position of the sensitive region.

47. The method of claim 41 further comprising using a processor for determining from the signals from the at least two receiver coils the parameter of interest of the earth formation.

48. A sensor assembly for nuclear magnetic resonance (NMR) measurements from a medium comprising:
(a) a U-shaped magnet including a pair of magnets having opposed magnetization coupled by a permeable yoke which provides a static magnetic field in a sensitive region in the medium;
(b) a transmitter coil producing a pulsed radio frequency (RF) magnetic field in said sensitive region;
(c) a field shifting magnet which alters a position of the sensitive region; and,
(d) at least one receiver coil for receiving signals from nuclei in said sensitive region, said at least one receiver coil having an axis substantially parallel to an axis of said transmitter coil.

49. A method of determining a parameter of interest of a medium comprising:
(a) using a U-shaped magnet including a pair of magnets with opposed polarization coupled by a magnetically permeable yoke for producing a static magnetic field in a sensitive region in the medium;
(b) using a transmitter coil for producing a pulsed radio frequency (RF) magnetic field in said sensitive region;
(c) using a field shifting magnet to alter a position of the sensitive region; and,
(d) using at least one receiver coil having an axis substantially parallel to an axis of said transmitter coil for receiving signals from nuclei in said sensitive region.

* * * * *